US007821564B2

United States Patent
Avron et al.

(10) Patent No.: US 7,821,564 B2
(45) Date of Patent: Oct. 26, 2010

(54) ASSEMBLY FOR ALIGNING AN OPTICAL SYSTEM

(75) Inventors: Jerome Avron, Haifa (IL); Zvika Gilad, Haifa (IL); Semion Khait, Tiberias (IL)

(73) Assignee: Given Imaging Ltd., Yoqneam Ilite (IL)

( * ) Notice: Subject to any disclaimer, the term of this patent is extended or adjusted under 35 U.S.C. 154(b) by 1052 days.

(21) Appl. No.: 11/020,308

(22) Filed: Dec. 27, 2004

(65) Prior Publication Data

US 2005/0179805 A1 Aug. 18, 2005

Related U.S. Application Data

(60) Provisional application No. 60/532,925, filed on Dec. 30, 2003.

(51) Int. Cl.
*H04N 5/225* (2006.01)
*H04N 3/14* (2006.01)

(52) U.S. Cl. .................. 348/340; 348/360; 348/374; 359/819

(58) Field of Classification Search .......... 348/340, 348/345, 347, 357, 360, 373–375; 359/818, 359/828, 829
See application file for complete search history.

(56) References Cited

U.S. PATENT DOCUMENTS

| 5,400,072 | A | * | 3/1995 | Izumi et al. ............... 348/335 |
| 5,604,531 | A | | 2/1997 | Iddan et al. |
| 5,691,853 | A | * | 11/1997 | Miyano ..................... 359/740 |
| 5,929,901 | A | | 7/1999 | Adair et al. |
| 6,043,839 | A | | 3/2000 | Adair et al. |
| 6,304,390 | B1 | * | 10/2001 | Takanashi ............. 359/699 |
| 6,335,759 | B1 | * | 1/2002 | Harada ................. 348/373 |
| 6,384,397 | B1 | * | 5/2002 | Takiar et al. ........ 250/208.1 |
| 6,741,286 | B2 | * | 5/2004 | Meek et al. ............ 348/370 |
| 6,939,295 | B2 | * | 9/2005 | Yokoi et al. ........... 600/176 |
| 2002/0135694 | A1 | * | 9/2002 | Williams ............... 348/375 |
| 2002/0195546 | A1 | | 12/2002 | Yamaguchi et al. |
| 2003/0158503 | A1 | | 8/2003 | Matsumoto |
| 2003/0171648 | A1 | | 9/2003 | Yokoi et al. |
| 2003/0171649 | A1 | | 9/2003 | Yokoi et al. |
| 2003/0171652 | A1 | | 9/2003 | Yokoi et al. |
| 2004/0027459 | A1 | | 2/2004 | Segawa et al. |
| 2004/0080658 | A1 | * | 4/2004 | Cambou et al. ........ 348/340 |

FOREIGN PATENT DOCUMENTS

| JP | 5745833 | 3/1982 |
| JP | 4180736 | 6/1992 |
| JP | 2001137182 | 5/2001 |
| JP | 2003260025 | 9/2003 |

* cited by examiner

*Primary Examiner*—David L Ometz
*Assistant Examiner*—Carramah J Quiett
(74) *Attorney, Agent, or Firm*—Pearl Cohen Zedek Latzer, LLP (57) ABSTRACT

A lens holder assembly for aligning an optical system over an image sensor is described. The image sensor may be lying on a substrate. The assembly may include a lens holder aperture and at least one centering leg or protrusion which may be detached from the substrate and wherein the centering legs or protrusions may tightly abut or surround the image sensor in order to center the lens holder assembly with respect to the image sensor and to the optical system.

12 Claims, 9 Drawing Sheets

ASSEMBLY FOR ALIGNING AN OPTICAL SYSTEM

PRIOR APPLICATION DATA

The present application claims benefit from prior U.S. provisional application No. 60/532,925 entitled "ASSEMBLY AND METHOD FOR ALIGNING AN OPTICAL SYSTEM" and filed on. Dec. 30, 2003, and incorporated herein by reference in its entirety.

FIELD OF THE INVENTION

The present invention relates to alignment, centering, and/or focal length positioning of an optical system, typically for use in an in vivo imaging device.

BACKGROUND OF THE INVENTION

Digital output image sensors, for example, CMOS image sensors, may provide a low cost and low energy consumption solution for miniature in-vivo imaging devices. In-vivo imaging devices incorporating image sensors, for example, ingestible imaging capsules are well known in the art. Generally, these devices may include, for example, an optical system associated with the imaging device, a light source to illuminate the in-vivo body lumen, and a lens holder for supporting the required optical system over the image sensor as well as for insulating the image sensor stray light that may originate from light sources. The optical system may be positioned at a height defined by the focal length and oriented over the image sensor so as to overlap a light sensing area of the image sensor. As a result of miniaturization, small errors in alignment of the optical system and lens holder with respect to image sensor due to, for example, variation of thickness of adhesives (for focal length) or improper centering of optical system and lens holder may affect the quality of images captured.

SUMMARY OF THE INVENTION

There is provided according to embodiments of the present invention, a lens structure and assembly method for aligning an optical system to an image sensor. According to embodiments of the present invention, the lens structure may contain for example an optical section and a structural section. The optical section may be for example an optical system and the structural section may extend from the optical section and include, for example, a stopper(s) for elevating the optical system a distance corresponding, for example, to a near optimal or optimal focal length distance. In some embodiments of the present inventions, a lip or other suitable structure may be provided on the lens structure that may abut at least two opposite sides or edges of the image sensor and center the lens structure with respect to the image sensor. In other embodiments of the present invention, a lens holder may be assembled onto the lens structure and the lens holder may secure the lens holder and lens structure assembly onto a substrate. In yet other embodiments of the present invention there is provided an assembly of two or more lens structures that may be stacked one on the other.

BRIEF DESCRIPTION OF THE DRAWINGS

The present invention will be understood and appreciated more fully from the following detailed description taken in conjunction with the drawings in which.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

Figure 1:
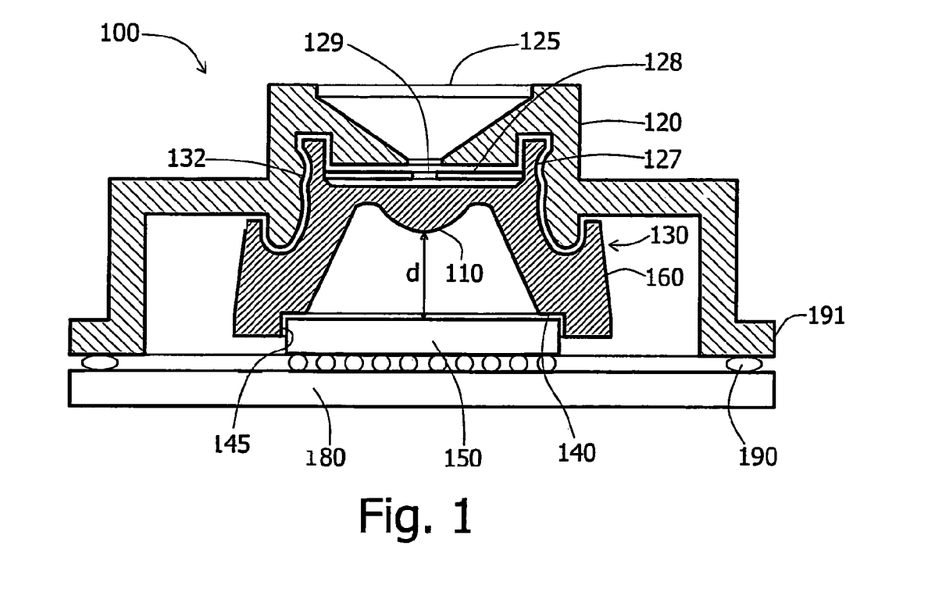
FIG. 1 shows schematically a cross-sectional view of a lens structure and lens holder for positioning an optical system over an image sensor according to an embodiment of the present invention.
Figure 2:
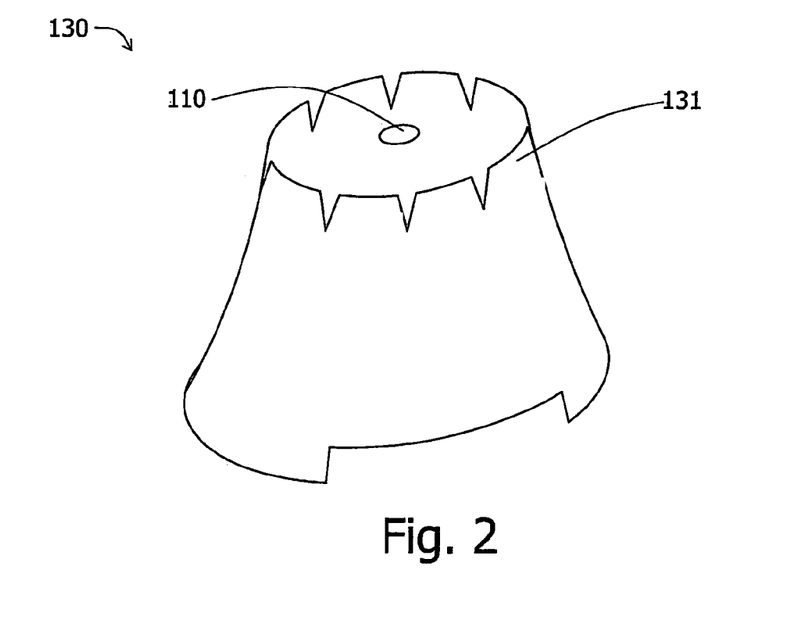
FIG. 2 shows a schematic isometric view of a lens structure according to another embodiment of the present invention.

Reference is now made to FIG. 1 showing an assembly 100 for positioning an optical system over and/or with respect to an image sensor according to an embodiment of the present invention. When used herein, terms like over, above, on, below, etc., are considered relative terms descriptive when a device is in a certain orientation relative to the viewer; it should be understood that these terms are relative, and given a certain orientation, an optical system may be "below" or "to the side of" an image sensor. Lens holder 120 together with lens structure 130 may be positioned over image sensor 150 and may be fixed and or secured with, for example, an adhesive 190 onto substrate 180 with, for example, one or more legs 191 of lens holder 120. Other fixing and securing methods, for example ultrasonic welding, may be used. An optional disk 128 with a disk aperture 129 substantially concentric with disk 128 may be positioned between lens holder 120 and lens structure 130 to, for example, control the amount of light penetrating to image sensor 150. Lens structure 130 may include an optical section, for example an optical system 110 and a structural section 160 extending from the optical section. Optical system 110 may include optical elements such as, for example, composite lenses, filters, and irises, and may be an integral part of lens structure 130. The structural section 160 of lens structure 130 may incorporate protrusion 127 for assembling lens structure 130 onto and/or over lens holder 120, stopper(s) 140 for setting and/or indicating the desired distance between the image sensor 150 and the optical system 110, and a protrusion, ledge or lip 145 for abutting lens structure to image sensor 150. In some embodiments of the present invention, the lip may extend beyond stopper 140. Protrusion(s) 127 may be adhered to lens holder 120 by, for example, gluing, friction fitting, press fitting, welding, laser welding, and/or other suitable methods. Other suitable surfaces, other than and/or in addition to protrusion 127 of lens structure 130 may be used to attach lens structure 130 to lens holder 120. Surfaces and or structures other than and/or in addition to stopper(s) 140 and lip 145 may be used to set and/or indicate the desired distance and centering position between image sensor 150 and optical system 110. In one embodiment of the present invention, an indentation 132 or other cavity, etc. may be added to lens holder 120, for example so that lens structure 130 may, for example, snap into place. In another embodiment of the present invention, protrusion 127 on lens structure 130 may include, for example, flexible leaves or sections 131 (FIG. 2) that may for example bend and at least partially come together when, for example, press-fitting protrusion 127 into lens holder 120. In one embodiment of the present invention, flexible leaves 131 may, for example bend in a range of degrees, as required, so as to allow for higher tolerances in the dimensions of lens protrusion 127 and lens holder 120. Other suitable methods may be used for assembling lens structure 130 with lens holder 120.

Protrusions 127 surrounding optical system 110 may also, for example, serve to protect optical system 110 from mechanical damage during, for example, packaging, delivery, handling, assembly, etc. Mechanical damage may include, for example, scratches, chips, smeared dirt, etc. on optical system 110.

Figure 3:
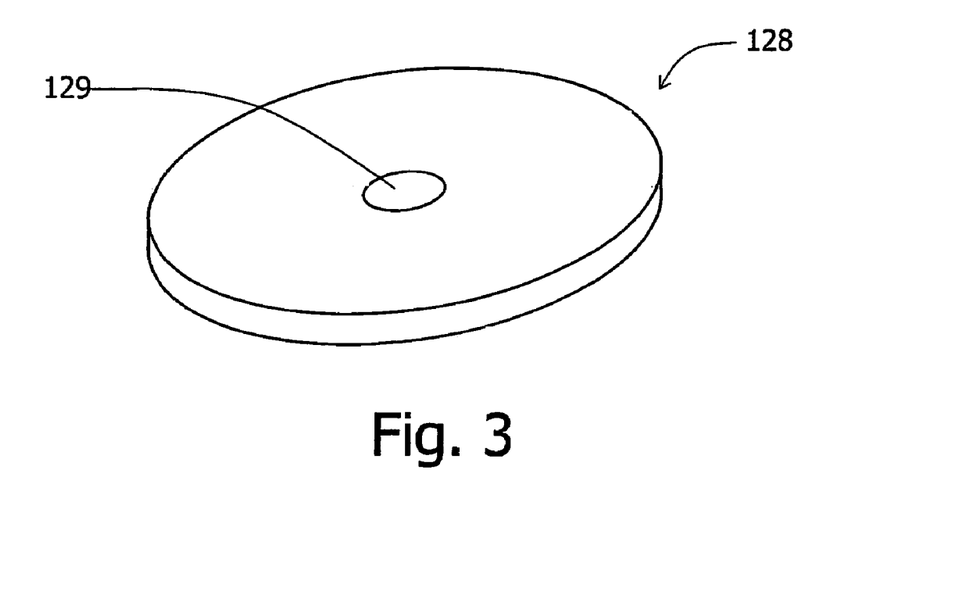
FIG. 3 shows a schematic isometric view of a disk with an aperature according to an embodiment of the present invention.

Lens holder aperture 125 may allow light reflected from an area of interest (not shown) to penetrate through optical system 110 toward image sensor 150. In another embodiment of the present invention, for example as shown in more detail in FIG. 3, a metal disk 128 with a hole, iris and/or disk aperture 129 substantially concentric with disk 128 may be included. Disk 128 with a disk aperture 129 may be manufactured and or fabricated, with a high degree of accuracy, as may be required, using well-known methods in the art, for example, etching and laser-cutting. Other suitable manufacturing processes may be used as well. The disk 128 may be made from for example black plated stainless steel. Other suitable materials, for example other metals, with other suitable types of plating or coating or with no plating may be used as well. The disk may be colored in any suitable way besides plating. In one embodiment of the invention, disk 128 may be assembled between lens structure 130 and lens holder 120, such that for example, protrusions 127 may support the disk 128. Other suitable methods of assembly may be used. Disk 128 with disk aperture 129 may provide the aperture for image sensor 150, with dimensions meeting the required accuracy. As such lens holder aperture 125 included in lens holder 120, preferably made from a plastic material and manufactured, for example, by injection molding, may be manufactured, in one embodiment of the present invention with a larger diameter and with a larger tolerance and not necessarily act as the aperture controlling light penetration toward the imager.

Lens structure 130 may be for example made and/or fabricated by a single mold for example by injection molding. Other suitable manufacturing procedures may be used as well. Lens structure 130 may be designed with a structural section 160, which may include one or more surfaces that may act as a stopper(s) 140. Stopper(s) 140 may limit the proximity of and/or distance the optical system 110 from image sensor 150 such that when stopper or stoppers 140 rest against image sensor 150, the optical system 110 and image sensor 150 may be at, for example, a near optimal or optimal focal length distance (e.g., distance d), or another desired distance. In one embodiment of the present invention, stopper(s) 140 may be in the form of two or more legs that may, for example, at least partially (or completely) rest over a non-light sensitive area of the image sensor surface, e.g. two or more corners of the image sensor. In an alternate embodiment, stopper(s) 140 may be of other suitable shapes or forms. As such, optical system 110 may be easily aligned in focal distance with respect to an image sensor 150 while avoiding tolerances in distance between optical system 110 and image sensor 150 that may otherwise occur due to glued or otherwise assembled parts between image sensor 150 and optical system 110, or other sources of tolerances. Lens holder 120 incorporating lens structure 130 may be fitted over, for example, a substrate 180, e.g. a Printed Circuit Board (PCB), in, for example, appropriate notches and may, for example be pressed down until stopper(s) 140 comes into contact with image sensor 150. Contact may be maintained, for example, by applying glue 190, screws (not shown), pins, or other connecting or adhering means. Alternatively, lens holder 120 and/or lens structure 130 may be connected to substrate 180 using other suitable component or surfaces.

Figure 4:
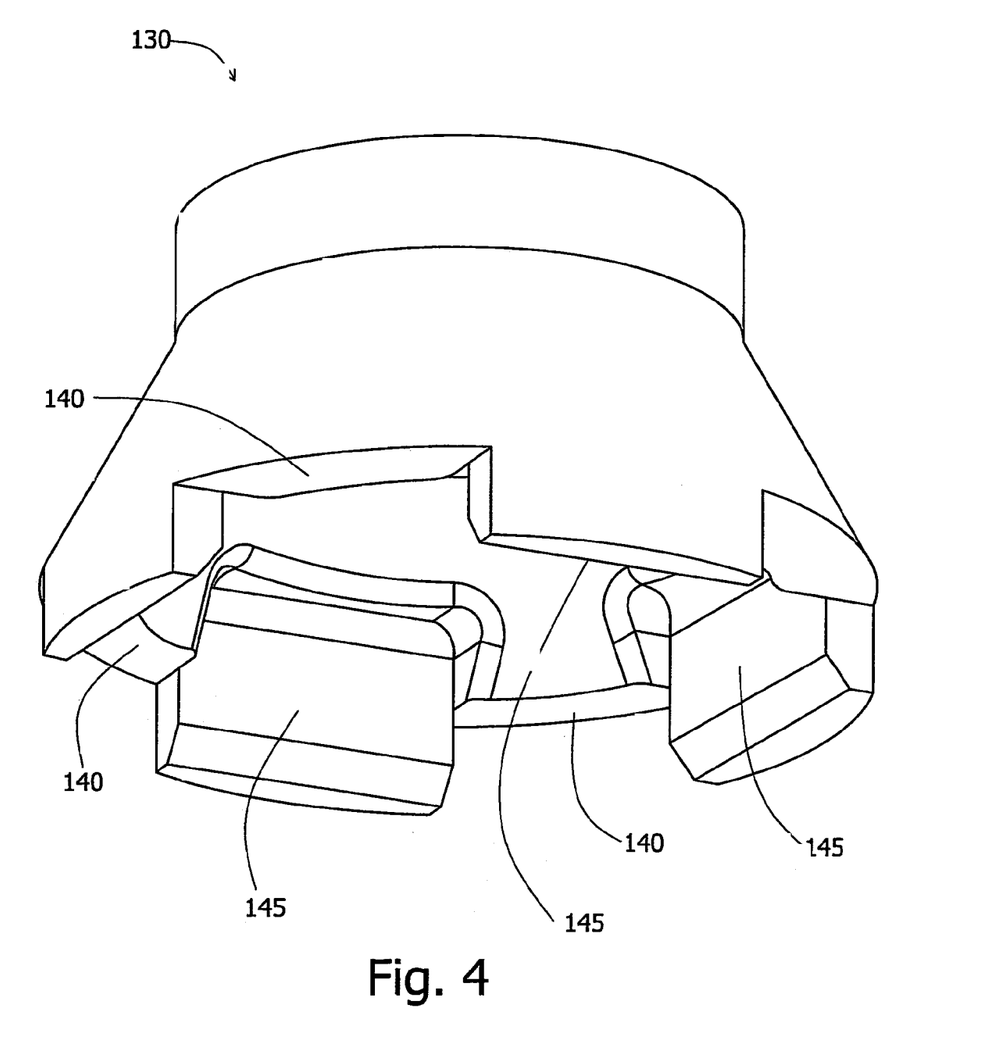
FIG. 4 shows a schematic isometric view of a lens structure according to an embodiment of the present invention.

In another embodiment of the present invention, lens structure 130 may include at least two abutting surfaces or lips 145, which may be, for example, four protrusions or lips that may abut, for example, opposite sides, corners, and/or points of a rectangular image sensor, or for example, each side or corner of a rectangular image sensor 150. Abutting lips 145 may be centered with respect to the optical system 110 and when fitted around image sensor 150, may center optical system 110 over image sensor 150. Other number of legs, a circular fence, or other suitable abutting surfaces may be used. In some embodiments of the present invention, lip 145 may be a single protrusion that may be substantially concentric with optical section 110 and may fit partially around image sensor 150 substantially concentrically. In other embodiments the lip 145 may be constructed from more than one protrusion. Reference is now made to FIG. 4 showing an isometric view of lens structure 130 according to an embodiment of the invention. In one embodiment of the present invention, lens structure 130 may include stopper(s) 140 that may be for example, in the form of four flat surfaces that may sit over image sensor 150 and four legs and/or lips 145 that may, for example, abut four sides of image sensor 150 for the purpose of centering optical system 110 over image sensor 150. Other suitable numbers of lips 145 and stoppers 140 may be used.

Figure 5:
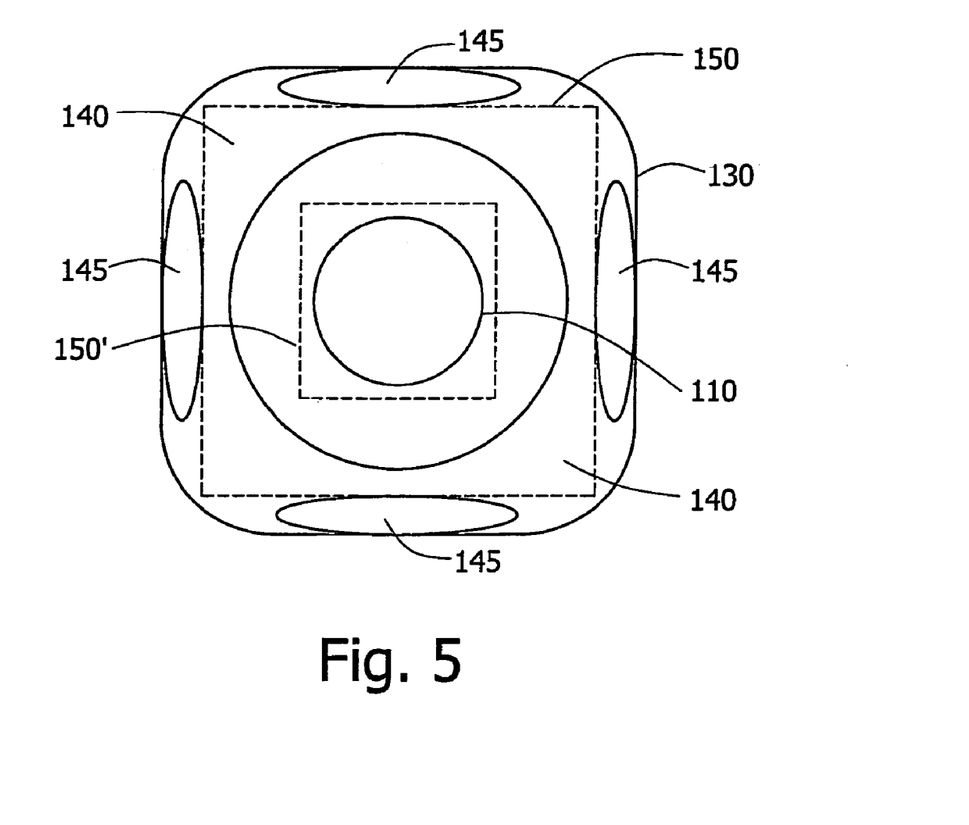
FIG. 5 shows schematically a bottom view of a lens structure according to an embodiment of the present invention.

FIG. 5 shows a schematic illustration of a bottom view of lens structure 130 where the dimensions of the perimeter of image sensor 150 are marked by a dotted line. According to one embodiment, the area around the perimeter of image sensor 150 may not be light sensitive and may, for example include circuitry and a central area 150' may include a light sensitive area (e.g., an area containing pixels). In this view abutting lips 145 may be seen as abutting the four sides of image sensor 150 according to an embodiment of this invention. In addition, stopper(s) 140 may be seen to at least partially overlap the four corners of image sensor 150 according to an embodiment of the present invention. In other embodiments stopper(s) 140 may overlap two or more corners or sections of image sensor 150.

In one embodiment of the present invention lens structure 130 may be made for example from a suitable silicon material or a transparent plastic, such as for example thermoplastic rigid polyurethane resins (e.g. isoplast™), Acrylonitrile-Butadiene-Styrene (ABS) copolymers, polycarbonates or other suitable materials. Lens structure 130 may be manufactured by, for example, injection molding. In an alternate embodiment of the present invention, lens structure 130 may be manufactured and/or fabricated by 2K injection molding where, as a first step for example, an opaque material such as any of the materials mentioned herein which may include a suitable color, may be injected in a mold in, for example, an area of the structural section 160 e.g. the surrounding wall of lens structure 130, and as a second step for example, a transparent material may be injected into for example the area in the mold of the optical system 110. As such the structural section 160 of the lens structure 130 may be fabricated from an opaque material while the optical system may be fabricated from a transparent material. In another embodiment of the invention the steps may be of a different order or more steps may be added. As such, according to an embodiment of the invention, lens structure 130 may have an opaque section that isolates the image sensor from surrounding stray light and a transparent section that includes for example optical system 110.

Figure 6:
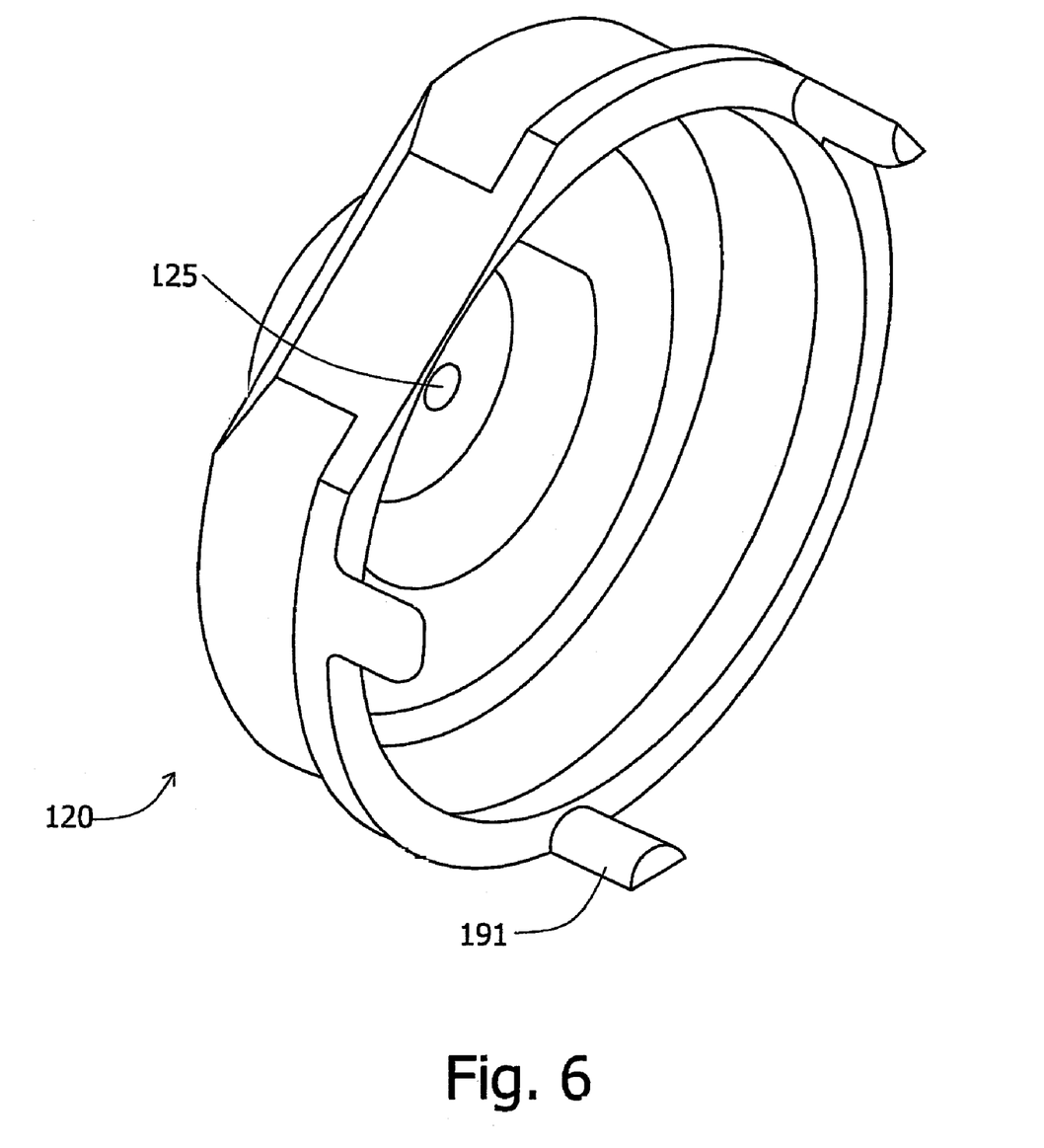
FIG. 6 shows schematically an isometric view of a lens holder according to an embodiment of the present invention.

Reference is made to FIG. 6 that schematically illustrates a lens holder according to embodiments of the present invention. Lens holder 120 may be made from any suitable plastic, e.g. ABS, and manufactured by, for example injection, molding or other suitable methods. In some embodiments of the present invention, lens holder 120 may be opaque or non-transparent so that light may not penetrate through the lens holder 120 other than through lens holder aperture 125. In other embodiments of the present invention, lens holder 120 may be of a transparent material. Other suitable materials or methods may be used to manufacture lens holder 120. Legs 191 may be used to position lens holder 120 in suitable notches on PCB and/or substrate 180.

Figure 7A:
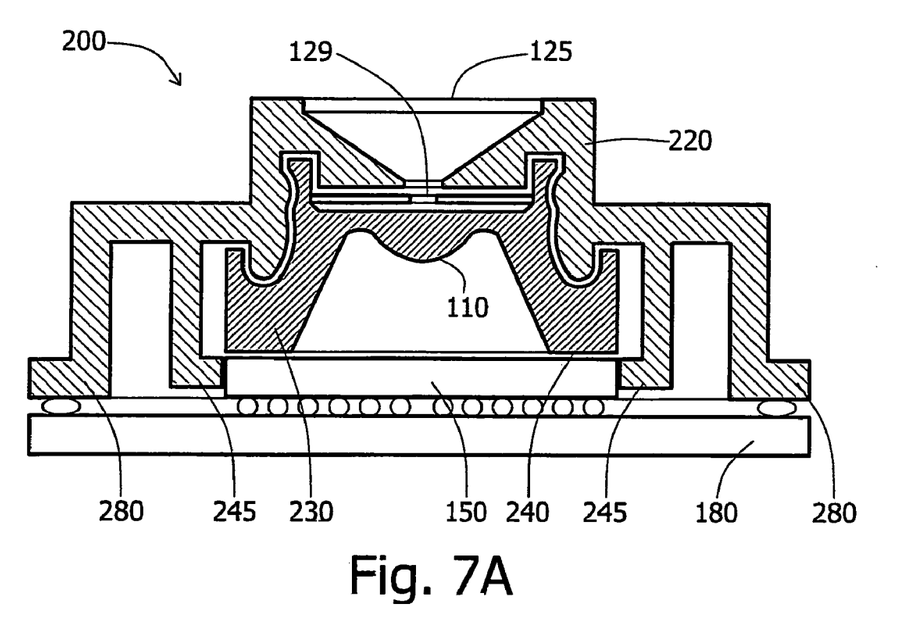
FIG. 7A shows schematically a cross-sectional view of a lens structure and lens holder for aligning an optical system over an image sensor according to another embodiment of the present invention.
Figure 7B:
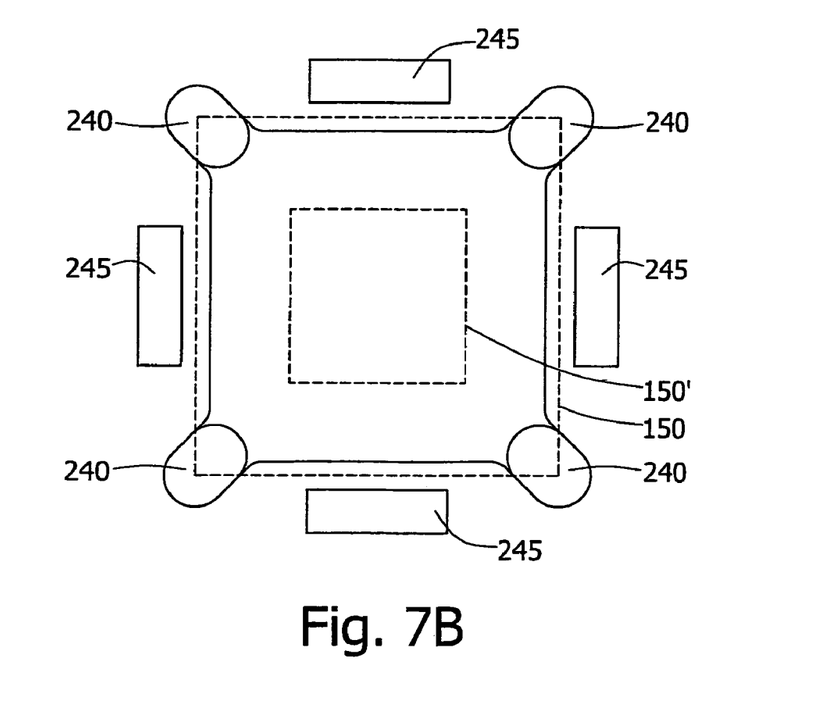
FIG. 7B shows schematically a bottom view of a lens structure and lens holder for aligning and centering an optical system over an image sensor according to an embodiment of the present invention.
Figure 7C:
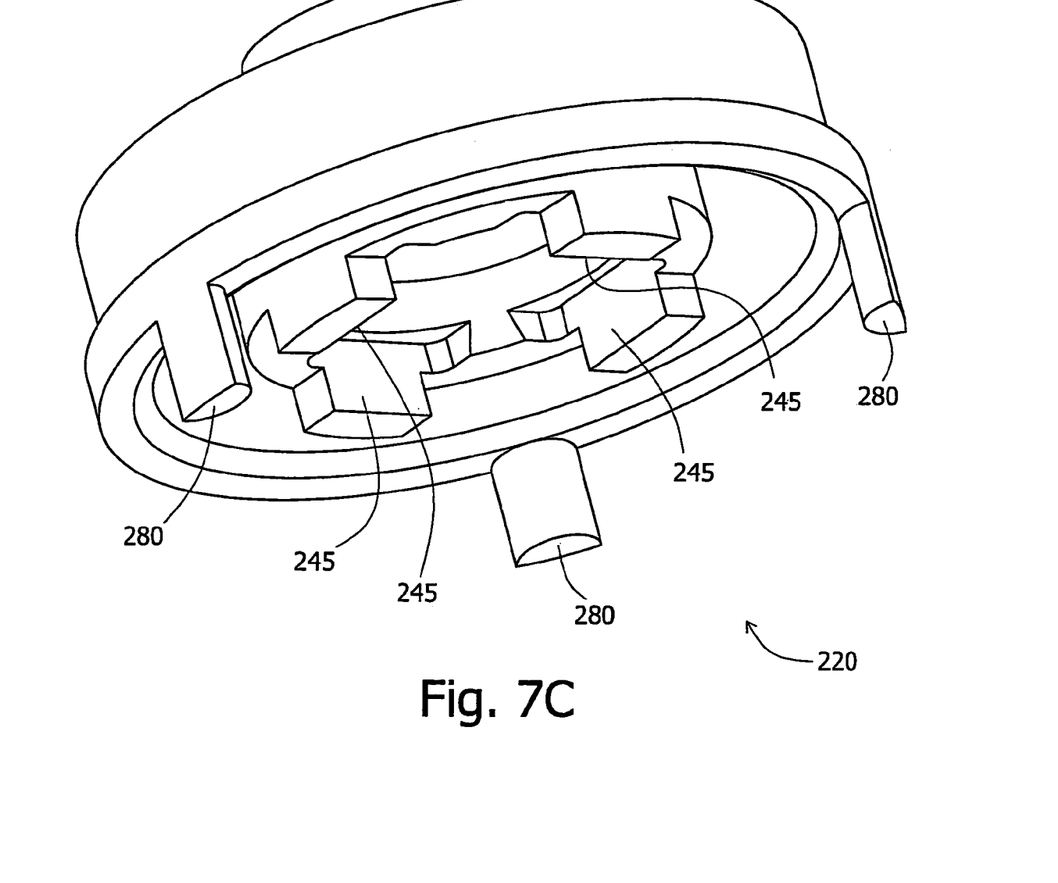
FIG. 7C shows an isometric view of a lens holder according to another embodiment of the present invention.

Reference is now made to FIGS. 7A-C schematically illustrating a lens structure and lens holder assembly according to an alternate embodiment of the present invention. FIG. 7A shows a cross-sectional view of a lens structure and lens holder assembly 200 for aligning and centering an optical system over an image sensor according to an alternate embodiment of the present invention. Lens holder 220 may include protrusions such as centering legs 245 that may, for example, be centered with respect to lens holder aperture 125 used to center image sensor 150 with respect to optical system 110. For example, at least two centering legs 245 may be used that may abut, for example, opposite sides of the image sensor. Centering legs 245 may or may not be in contact with a surface 180. In some embodiments of the present invention, centering legs 245 may be a single protrusion that may be substantially concentric with aperture 129 and may fit at least partially around image sensor 150 substantially concentrically. In other embodiments the lip 145 may be constructed from more than one protrusion. Lens structure 230 may have stopper(s) 240 that may limit the proximity of optical system 110 to image sensor 150 such that when stopper(s) 240 rest against image sensor 150, the optical system 110 and image sensor 150 may be at a near optimal focal distance, an optimal focal distance, and/or any other suitable predetermined distance. According to some embodiments, the lens holder 220 may include periphery legs 280 that may be secured to a surface 180, e.g. a PCB or other components surfaces or structures with for example glue, screws, or any other suitable securing method and/or periphery legs 280 may be positioned within suitable notches in support 180. FIG. 7B shows a bottom view of lens structure 230, lens holder 220, and an outline of the perimeter of image sensor 150 indicated by a dotted line. In this view lens holder centering legs 245 may abut, for example, four sides of image sensor 150 according to an embodiment of this invention. Stopper(s) 240 may at least partially overlap, for example two to four corners of image sensor 150 according to an embodiment of the present invention. Each of stopper(s) 240 and centering leg 245 may in other embodiments of the invention include a different suitable number of surfaces or legs and the surfaces and/or legs may be of any suitable size. Stopper(s) 240 may partially overlap image sensor 150 in a suitable location other than the corners of image sensor 150.

Reference is now made to FIG. 7C showing an isometric view of lens holder 220 with four centering legs 245. In one embodiment of the invention lens holder 220 may have periphery legs 280 that may be secured to a support 180, for example a PCB, or other components, surfaces, or structures with for example glue, screws, or any other suitable securing method. In an alternate embodiment, lens holder 220 may not include periphery legs 280 and centering legs 245 may be directly secured or fastened to, for example, a PCB 180, structure, or component with for example glue, screws, or any other suitable securing method.

Figure 8:
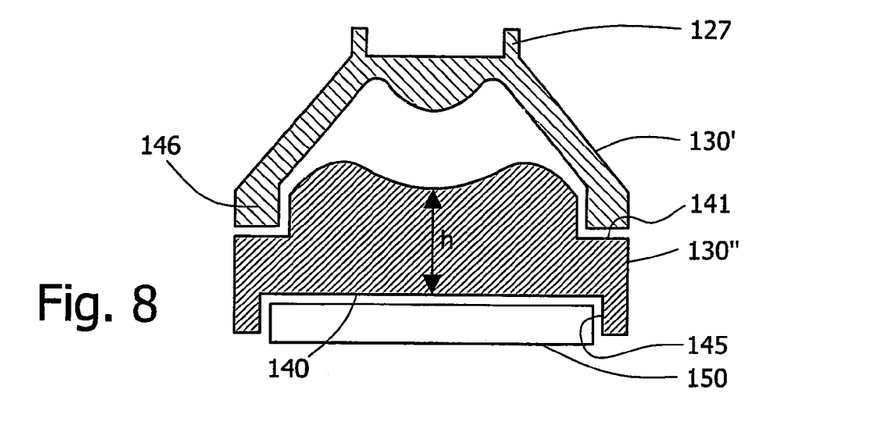
FIG. 8 shows schematically a cross-sectional view of a two lens structure assembly positioned over an image sensor according to an embodiment of the present invention.

Reference is now made to FIG. 8 showing a two lens structure assembly positioned over an image sensor according to embodiments of the present invention. In one embodiment of the present invention, a first lens structure 130' incorporating a first optical system 110 may directly sit on a step(s) 141 of a second lens structure 130" that may incorporate a second optical system 112. Lens structure 130" may, for example, sit directly over an image sensor 150. In other embodiments of the present invention, lens structure 130" may include a stopper such as stopper(s) 140 shown in FIG. 1 and only the stopper(s) 140 may sit directly on the image sensor 150. The geometry of lens structures 130' and 130" may set and/or define the desired distances, e.g. focal length distance, between optical systems 110 and 112 and image sensor 150 during assembly. For example, lens structure legs 146 of lens structure 130' and step(s) 141 of lens structure 130" may determine the distance between optical system 110 and optical system 112 while the height "h" of lens structure 130" may determine the distance between optical system 112 and image sensor 150. In other embodiments other geometries of lens structures 130' and 130" may be used to define the distances between optical systems 110 and 112 and image sensor 150. In yet other embodiments of the present invention more than two lens structure may be directly or indirectly stacked or otherwise placed over each other. Stacking lens structures 130' and 130" directly over each other has the advantage of avoiding tolerances that might otherwise occur do to an assembly of multiple parts. For example, when assembling a first optical system on to a first lens holder and then stacking that first lens holder on another assembly of a second optical system assembled onto and second lens holder tolerances may accumulate between the assemblies of the lenses onto the lens holders in additions to the assembly of one lens holder onto another. Stacking lens structures 130' and 130" serves, for example to avoid tolerances due to the addition of lens holders.

In the embodiment shown in FIG. 8 lens structure 130' and 130" may be made and/or fabricated, for example, from a suitable silicon material or a transparent plastic, such as for example isoplast™, ABS, polycarbonates or other suitable materials. Lens structures 130' and 130" may be each be fabricated by, for example, a single mold using, for example, injection molding. In an alternate embodiment of the present invention, lens structures 130' and 130" may be manufactured by 2K injection molding where, as a first step for example, an opaque material such as any of the materials mentioned herein which may include a suitable color, may be injected in a mold in, for example, an area of the surrounding wall of lens structure 130, and as a second step for example, a transparent material may be injected into for example the area in the mold of the optical system 110 and/or optical system 112. In another embodiment of the invention the steps may be of a different order or more steps may be added. As such, according to an embodiment of the invention, lens structures 130' and 130" may have an opaque section that isolates the image sensor from surrounding stray light and a transparent section that includes, for example, optical system 110 and optical system 112. Lens structure 130' and lens structure 130" may be fixed onto each other by for example, gluing, friction fitting, press fitting, welding, laser welding, and/or other suitable methods. In other embodiments, lens structure 130' and 130" may simply be stacked one over the other and a lens holder, for example, a lens holder similar to lens holder 120 (FIG. 6) and/or lens holder 220 (FIG. 7C) may hold the lens structures 130' and 130" in place.

Figure 9:
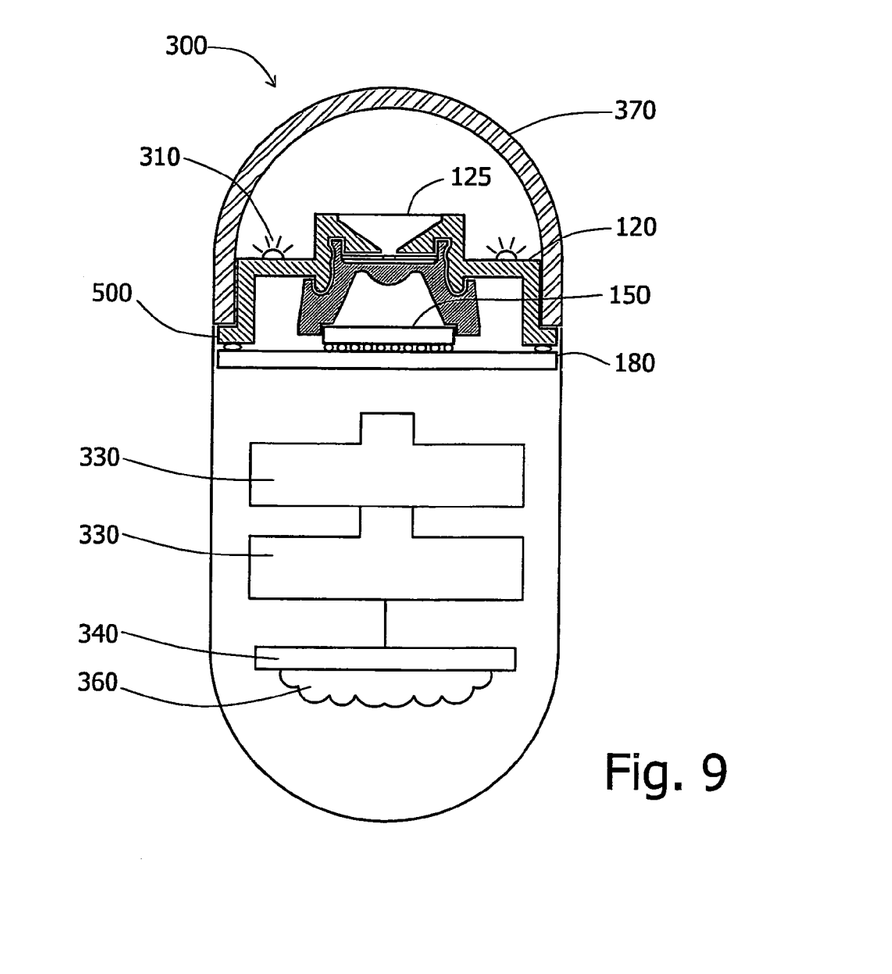
FIG. 9 shows schematically a lens structure and lens holder assembly incorporated in an in-vivo autonomous capsule according to an embodiment of the present invention.

According to one embodiment of the present invention a lens structure and lens holder assembly may be incorporated in an in-vivo device, as shown, for example, in FIG. 9. For example, an in-vivo device may be a swallowable capsule for imaging the gastrointestinal (GI) tract, an endoscope, a catheter, a stent, a needle or other suitable in-vivo devices. In one embodiment, the lens structure 130 and lens holder 120 may be incorporated into a swallowable imaging device, for example, as shown schematically in FIG. 9. An imaging capsule may be similar to embodiments described in International Application publication number WO 01/65995 entitled "A Device And System For In-vivo Imaging", published on 13 Sep. 2001, or embodiments described in U.S. Pat. No. 5,604,531 to Iddan et al., both of which are assigned to the common assignee of the present invention and which are hereby incorporated by reference. Device 300 may include according to an embodiment of the invention, lens structure 130 and lens holder 120, one or more illumination sources 310, and image sensor 150 that may sit on for example a PCB 180. Illuminating sources 310 may illuminate an in-vivo area of interest (not shown) through viewing dome 370 and image sensor 150 may sense light reflected from area of interest (not shown) that may penetrate through viewing dome 370 and lens structure 130 and lens holder 120, typically through disk aperture 129. Viewing dome 370 may be directly assembled and adhered to lens holder rim 500 of lens holder 120. As such the viewing dome 370 may be assembled substantially concentrically with respect to the lens holder 120, lens structure 130 and image sensor 150. Device 300 may further include one or more power sources 330, such as batteries, and a transmitter 340 with antenna 360 for transmission, such as by RF, of for example sensed and/or imaged data. Other suitable components may be included in device 300. In other embodiments, the lens structure 130 and lens holder 120 may be used with other imaging capsules or devices having other components and structures. For example, transmitter 340 may be positioned on PCB 180 and antenna 360 may be incorporated into lens holder 120.

According to one embodiment one or more illuminating sources 310, e.g. LEDs, may be positioned on the lens holder 120 (for example, as shown in FIG. 9), typically on a different plane than that of the image sensor 150. This arrangement may serve to reduce incident of stray light from illumination sources 310 onto image sensor 150. According to one embodiment illumination sources 310 may be electrically connected to power sources 330 through, for example, lens holder 120 and/or through PCB 180, for example, by wires running through lens holder 120 to PCB 180. According to other embodiments illumination sources 310 may be positioned otherwise, for example, directly on PCB 180. According to some embodiments lens holder 120 may be at least partially opaque or opaque in some parts so as to assist in reducing incident of stray light from illumination sources 310 onto image sensor 150.

Figure 10:
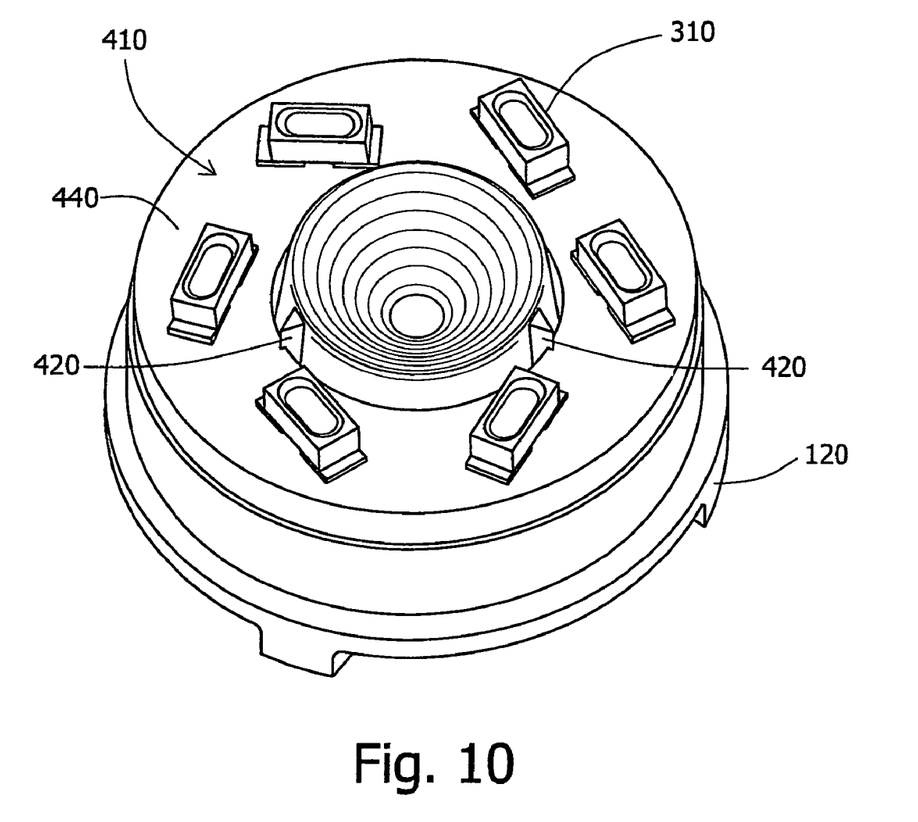
FIG. 10 shows schematically an illumination source assembled onto a lens holder according to an embodiment of the present invention.

Reference is now made to FIG. 10 showing an illumination source 310 in the form of an illuminating ring 410, e.g. a LED ring, positioned over the lens holder 120 and concentric to lens holder aperture 125, according to one embodiment. According to an embodiment of the present invention, illumination source 310 may be, for example, white LEDs, monochromatic LEDs, or other suitable LEDs. In one embodiment of the present invention, one or more illumination source(s) 310 may be, for example, mounted on a ring substrate 440 in the form of a ring. Two or more spikes 420 on lens holder 120 may secure the positioning and center the ring substrate 440 and illumination source(s) 310 with respect to the lens holder 120 and/or lens holder aperture 125. Since the lens holder 120 may be centered with respect to viewing dome 370 as described herein, the lens structure 130, the optical section 110, the aperture 129, the imager 150, and the Illuminating ring 410 may all be concentric with each other and with viewing dome 370.

Figure 11:
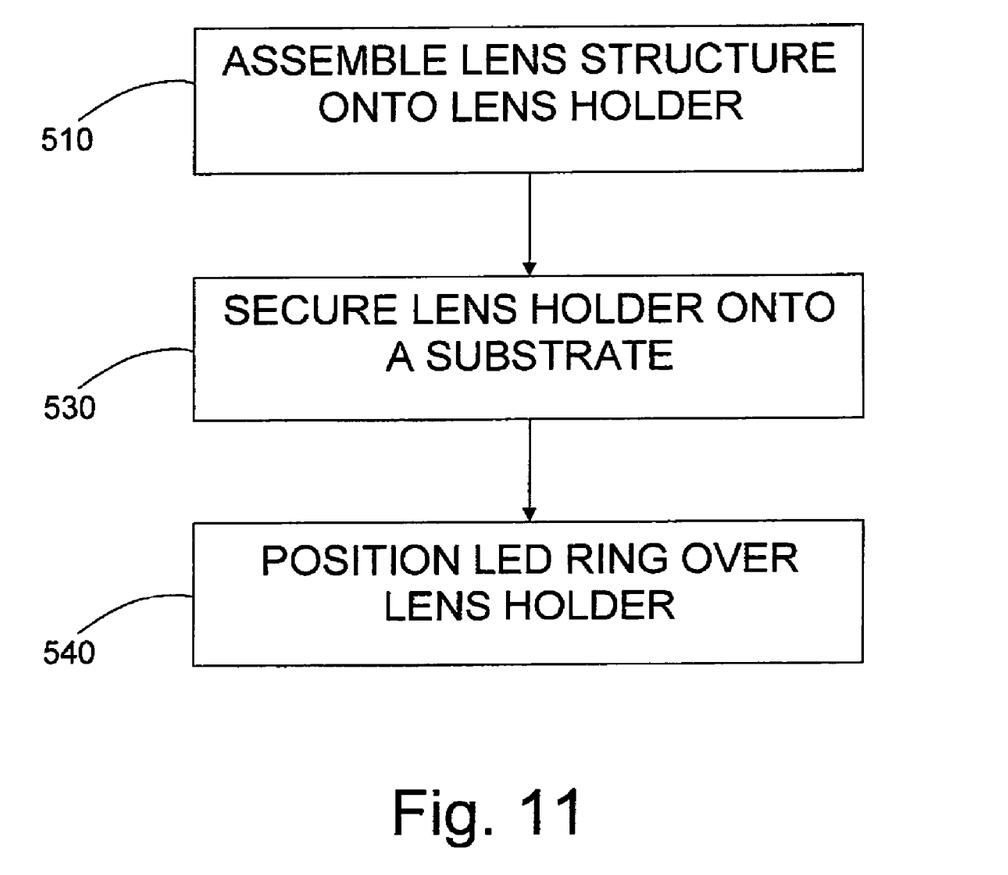
FIG. 11 shows a flow chart describing a method for aligning an optical system with respect to an imager sensor according to an embodiment of the invention.

Reference is now made to FIG. 11 showing a flow chart describing a method of aligning an optical system with respect to an imager sensor. In block 510 a lens structure, such as the lens structure 130 may be assembled onto a lens holder (e.g., lens holder120). According to embodiments of the present invention, the lens structure may be fabricated with, for example a single mold and may be fabricated from, for example, polyurethance resin. Other suitable materials may be used. According to embodiments of the present invention, the structural section 160 of lens structure 130 may incorporate, for example, protrusion 127 for assembling lens structure 130 onto and/or over lens holder 120. Protrusion(s) 127 may be, for example, adhered to lens holder 120 by, for example, gluing, friction fitting, press fitting, welding, laser welding, and/or other suitable methods. Other suitable surfaces, other than and/or in addition to protrusion 127 of lens structure 130 may be used to attach lens structure 130 to lens holder 120. In some embodiments of the present invention the metal disk 128 with the aperature 129 may be assembled onto lens structure 130, for example, within an area defined within the boundry of, for example, protursion 127. As such, lens structure 130 with disk 128 may be, for exampled assembled onto lens holder 120. In some embodiments, a surface, for example, a stopper(s) 140 may be used to set and/or indicate the desired distance between image sensor 150 and optical system 110. Stopper(s) 140 may overlap an area of the image sensor surface that may not be light sensitive.

In other embodiments, abutting lip(s) 145 may be concentric (and/or centered) with respect to the optical system 110 and when fitted around image sensor 150, may center optical system 110 over image sensor 150. In other embodiment the protrusion for centering may be integral to lens holder 120, for example, centering legs 245. In block 530 the lens holder 120 may be secured to a substrate 180. For example, lens holder 120 may be fixed and or secured with, for example, an adhesive 190 onto substrate 180 with, for example, one or more legs 191 of lens holder 120. Other fixing and securing methods, for example ultrasonic welding, may be used. In block 540 a LED ring may be positioned over the lens holder 120.

In one embodiment of the present invention, one or more illumination source(s) 310 may be, for example, mounted on a ring substrate 440 in the form of a ring. Two or more spikes 420 on lens holder 120 may secure the positioning and center the ring substrate 440 and illumination source(s) 310 with respect to the lens holder 120 and/or lens holder aperture 125. Since the lens holder 120 may be centered with respect to viewing dome 370 as described herein, the lens structure 130, the optical section 110, the aperture 129, the imager 150, and the illuminating ring 410 may all be concentric with each other and viewing dome 370.

It will be appreciated by persons skilled in the art that the present invention is not limited to what has been particularly shown and described hereinabove. Rather the scope of the present invention is defined only by the claims which follow.

The invention claimed is:

1. An optical lens aligning assembly for centering an optical lens over an image sensor, said image sensor lying on a substrate, and said optical lens aligning assembly comprising:
   a lens holder having an aperture; and
   a lens structure comprising (a) an integral section comprising the optical lens and (b) an integral structural section, said structural section comprising at least one lip detached from the substrate and tightly surrounding said image sensor to center the image sensor with respect to said optical lens section, and further comprising a protrusion for assembling said lens holder onto said lens structure so as to center said optical lens section with respect to said aperture, allowing light to pass through said aperture into said optical lens section.

2. The aligning assembly according to claim 1 wherein said at least one lip abuts the sides of the image sensor.

3. The aligning assembly according to claim 1 wherein the at least one lip is centered with respect to the lens holder aperture.

4. The lens assembly according to claim 1 wherein said lens holder further comprising at least one periphery leg, wherein said periphery leg is secured to the substrate.

5. The aligning assembly according to claim 1, wherein said at least one lip comprises at least two centering legs to tightly abut opposing edges of said image sensor to center the image sensor with respect to said optical lens section.

6. The aligning assembly according to claim 1 wherein the lens structure further comprises a stopper to set a distance of the optical lens section from the image sensor on which the stopper rests.

7. The aligning assembly according to claim 1 wherein the lens structure is fabricated by a single mold.

8. The aligning assembly according to claim 1 wherein the lens structure includes an opaque section and a transparent section.

9. The aligning assembly according to claim 1 comprising a metal disk disposed between the lens structure and the lens holder wherein the disk comprises a disk aperture substantially concentric with the lens holder aperture.

10. The assembly according to claim 1 comprising an illuminating ring wherein the illuminating ring is assembled over the lens holder and substantially concentric with the lens holder aperture.

11. The assembly according to claim 10 wherein the lens holder comprises a spike for centering the illuminating ring with respect to the lens holder aperture.

12. The assembly according to claim 1 wherein the lens holder comprises a rim configured for assembling a viewing dome concentrically over the lens holder.

* * * * *